United States Patent [19]

Amselem et al.

[11] 4,321,266

[45] Mar. 23, 1982

[54] 5-O-CYANOBENZYL-4,5,6,7-TETRAHYDRO-THIENO [3,2-C] PYRIDINE

[75] Inventors: Armand Amselem, Toulouse; Fernand Eloy, Eaunes; Jean-Pierre Maffrand, Portet, all of France

[73] Assignee: Sanofi, Paris, France

[21] Appl. No.: 193,907

[22] Filed: Oct. 6, 1980

[51] Int. Cl.$^3$ .................. C07D 495/04; A61K 31/395
[52] U.S. Cl. .................... 424/246; 546/114
[58] Field of Search ........................ 546/114; 424/256

[56] References Cited

U.S. PATENT DOCUMENTS

| | | | |
|---|---|---|---|
| 4,051,141 | 9/1977 | Castaigne | 546/114 |
| 4,075,340 | 2/1978 | Maffrand | 546/114 X |
| 4,076,819 | 2/1978 | Maffrand | 546/114 X |
| 4,097,482 | 6/1978 | Amselem | 546/114 OR |
| 4,104,390 | 8/1978 | Ferrand et al. | 546/114 X |

FOREIGN PATENT DOCUMENTS 2404308  2/1978  Fed. Rep. of Germany .

OTHER PUBLICATIONS

Maffrand et al., *Eur. J. Med. Chem.—Chemica Therapeutica,* Sep.–Oct. 1974, vol. 9, No. 5, pp. 483–486.
Podesta et al., *Eur. J. Med. Chem.—Chemica Therapeutica,* Sep.–Oct. 1974, vol. 9, No. 5, pp. 487–490.

*Primary Examiner*—John M. Ford
*Attorney, Agent, or Firm*—Weiser, Stapler & Spivak

[57] ABSTRACT

The free base, 5-o-cyanobenzyl-4,5,6,7-tetrahydro-thieno [3,2-c] pyridine, a method for the preparation thereof, therapeutic compositions having blood-platelet aggregation inhibiting activity, therapeutic dosage units of the compositions, and a method for the treatment of warm-blooded animals to inhibit blood platelet aggregation, are described.

4 Claims, No Drawings

5-O-CYANOBENZYL-4,5,6,7-TETRAHYDRO-THIENO [3,2-C] PYRIDINE

The present invention relates to the free base 5-o-cyanbenzyl-4,5,6,7-tetrahydrothieno [3,2-c] pyridine.

THE PRIOR ART

The synthesis of therapeutically interesting 5-benzyl-4, 5, 6, 7-tetrahydrothieno [3,2-c] pyridines and certain acid addition salts thereof such as the chlorohydrates and maleates, was described by J. P. Maffrand and F. Eloy in *Eur. J. Med. Chem.—Chimica Therapeutica*, September-October 1974–9; No. 5, p. 483–486.

The anti-inflammatory activity and activity in the inhibition of blood-platelet aggregation of certain 5-benzyl-4,5,6,7-tetrahydrothieno [3,2-c] pyridines substituted on the phenyl nucleus was disclosed by M. Podesta, D. Aubert and J. C. Ferrand in *Eur. J. Med. Chem.—Chimica Therapeutica*, September-October 1974–9, No. 5, p. 487–490.

German Patentschrift No. 24 04 308, issued Feb. 9, 1978, describes a large number of 4,5,6,7-tetrahydrothieno [3,2-c] derivatives and acid addition salts thereof, which have anti-inflammatory activity and activity for the inhibition of blood-platelet aggregation.

Castaigne U.S. Pat. No. 4,051,141 issued Sept. 27, 1977 discloses many 5-benzyl-4,5,6,7-tetrahydrothieno [3,2-c] pyridines having various substituents on the benzyl group, and the acid addition salts thereof, primarily the hydrochlorides, which also have inhibitor action on blood-platelet aggregation and anti-inflammatory activity. These derivatives also exhibit peripheral and cerebral vasodilator action and anti-arrhythmic action.

Amselem U.S. Pat. No. 4,097,482 issued June 27, 1978 describes a class of ortho-substituted 5-benzyl-4,5,6,7-tetrahydrothieno [3,2-c] pyridines and the hydrochloride, fumarate and maleate acid addition salts thereof which have the same combination of inhibitor action against blood-platelet aggregation and anti-inflammatory activity as the other prior art referred to above. These derivatives also exhibit peripheral and cerebral vasodilator action. Derivative No. 7 of this patent, 5-o-cyanobenzyl-4,5,6,7-tetrahydrothieno [3,2-c] pyridine maleate is the closest previously known derivative to the novel base of the present invention, since it is the maleate acid addition salt thereof.

SUMMARY OF THE INVENTION

The present invention relates to a single compound, the free base 5-o-cyanobenzyl-4,5,6,7-tetrahydrothieno [3,2-c] pyridine.

As noted above U.S. Pat. No. 4,051,141 issued Sept. 27, 1977 to Castaigne (Castaigne '141) and U.S. Pat. No. 4,097,482 to Amselem (Amselem '482), Jan. 27, 1978, disclose slats of pyridine derivatives, including other salts of the 5-o-cyanobenzyl-4,5,6,7-tetrahydrothieno [3,2-c] pyridine free base which was not itself disclosed therein.

The new base, like the derivatives of the Castaigne '141 and Amselem '482 patents referred to above, exhibits excellent inhibitor action on blood-platelet aggregation in warm-blooded animals including humans.

PREPARATION OF THE BASE

The free base of the present invention is prepared according to the general procedures of the prior art referred to above and, in particular according to the procedures of Castaigne U.S. Pat. No. 4,051,141 and Amselem U.S. Pat. No. 4,097,482, the entire disclosure of each of which is incorporated herein by reference. While the derivatives of the prior art were obtained directly as the salts, the free base of the present invention is available directly or from its salts by conventional techniques well-known in the art.

The free base, prepared according to the procedures of the prior patents, has the empirical formula $C_{15}H_{14}N_2S$, has a molecular weight of 254.6, and is obtained as white crystals having a melting point of 70° C. when cristallized from isopropanol.

The free base has very low toxicity comparable to that of its salt for which the results of toxicological and pharmacological tests are reported in our application Ser. No. 193,906, filed Oct. 10, 1980 which is incorporated herein by reference.

INHIBITOR ACTION ON BLOOD-PLATELET AGGREGATION

The inhibitor action on blood-platelet aggregation of the base of the present invention was determined by two different standard methods known to the art.

The first method, involving the use of ADP (adenosine diphosphate), is that of FERRAND, J. C.; GAICH, C., GULLY, D.; DUMAS, A.—EVALUATION DE L EFFET ANTI-AGREGANT DE LA TICLOPIDINE PAR UNE TECHNIQUE SUR SANG TOTAL. COMM. SOCIETE DE BIOLOGIE DE TOULOUSE (TOULOUSE 9 FEVRIER 1978), RESUME IN: REV MED TOULOUSE, 1978, 14, (SUPPL. 5) 680, referred to hereinafter as the ADP method.

The second method is that described in FERRAND, J. C.; LALE, A.—NUMERATION ET AGREGATION PLAQUETTAIRE A L' AIDE DE L' AUTOCOUNTER. APPLICATION A L' ETUDE DE LA TICLOPIDINE. COMM. SYMPOSIUM TECHNICON INDUSTRIE (PARIS, 15 JUIN 1978); FERRAND, J. C., LALE, A.,—EVALUATION EX-VIVO DE L' AGREGATION PLAQUETTAIRE PAR UNE TECHNIQUE AUTOMATIQUE SUR SANG TOTAL COMM. SOCIETE FRANCAISE DE BIOLOGIE CLINIQUE (PARIS 28 SEPTEMBRE 1979); and J. C. FERRAND, A. LALE, D. AUBERT ET G. BARTHELEMY—APPRECIATION QUANTITATIVE DE L' ACTIVITE ANTIAGREGANTE DE LA TICLOPIDINE PAR VOIE AUTOMATIQUE. COMM. REUNION DE L' ASSOCIATION FRANCAISE DE PHARMACOLOGISTES DIJON (2–3 MAI 1980), and is referred to hereafter as the collagen method.

Groups of 10 female rats of the Wistar type were each dosed with the base or one of the salts of the invention and with the corresponding maleate salt of Amselem U.S. Pat. No. 4,097,482, at periods of 48 hours, 24 hours and 2 hours prior to drawing blood for testing by the ADP and collagen techniques referred to above. The active medicament was administered by means of a gastric tube in the form of a 5% aqueous solution of gum arabic at a dosage level of 100 mg/Kg. The results are as follows.

| | BLOOD PLATELET AGGREGATION | | |
|---|---|---|---|
| | ADP | | |
| MEDICAMENT TESTED | 1 mn 30 s | 3mn | COLLAGEN |
| Controls | 0.29 | 0.40 | 2.53 |
| Base | 0.77 | 0.84 | 0.62 |

The free base shows substantial inhibitory activity against blood-platelet aggregation in rats. The base is generally less stable and less soluble then the salts. The base is, however, especially valuable as an intermediate in making certain preferred salts disclosed in our application Ser. No. 193,906, filed Oct. 10, 1980.

The base of the present invention, may be administered by any route known to the prior art to be suitable for such drugs, and specifically as directed in the Castaigne '141 and Amselem '482 patents, for all routes and purposes disclosed therein. More specifically, while the compounds and salts of the prior art are generally administered in dosages from about 0.25 g to about 1 g of active medicament per day (or up to 3 g for vasodilator action), the base may be used in amounts of up to about 1.5 g or even more per day for the utilities described.

The base like the derivative of the prior art, may be formulated for oral administration as tablets, coated tablets, capsules, drops or syrups with the usual pharmaceutically acceptable carriers, including excipients or adjuvants. As shown above, a preferred dosage unit is a capsule containing about 175 mg or somewhat less, of the base alone or with any desired pharmaceutically acceptable carrier. The new base may also be formulated as suppositories for rectal administration or in injectable solutions for parenteral administration.

Non-limiting examples of suitable dosage forms are set forth in the Castaigne '141 and Amselem '482 patents, for the various utilities described therein, and such forms and dosages are appropriate with routine adjustment as known by one skilled in the art to provide lower levels of the base equivalent to the known dosage levels of the derivatives of the base.

What is claimed is:

1. The free base, 5-o-cyanobenzyl-4,5,6,7-tetrahydrothieno [3,2-c] pyridine.

2. The therapeutic composition having blood-platelet aggregation inhibiting activity which comprises the base of the claim 1 in a pharmaceutically acceptable carrier.

3. A therapeutic dosage unit comprising the composition of claim 2 and containing from about 0.025 g to about 5 g of said base.

4. A method for the treatment of a warm-blooded animal to inhibit blood-platelet aggregation which comprises administering the composition of claim 2 to said animal in an amount effective to inhibit blood-platelet aggregation.

* * * * *